United States Patent
Meffin et al.

(10) Patent No.: US 9,517,345 B2
(45) Date of Patent: Dec. 13, 2016

(54) NEUROPROSTHETIC STIMULATION

(71) Applicants: National ICT Australia Limited, Eveleigh, NSW (AU); The University of Melbourne, Parkville, Victoria (AU)

(72) Inventors: Hamish Meffin, Parkville (AU); Anthony Burkitt, Parkville (AU); David Grayden, Parkville (AU); Behman Tayahori, Parkville (AU); Elma O'Sullivan Greene, Parkville (AU)

(73) Assignee: NATIONAL ICT AUSTRALIA LIMITED, Eveleigh, New South Wales (AU)

( * ) Notice: Subject to any disclaimer, the term of this patent is extended or adjusted under 35 U.S.C. 154(b) by 0 days.

(21) Appl. No.: 14/763,402

(22) PCT Filed: Jan. 28, 2014

(86) PCT No.: PCT/AU2014/000050
§ 371 (c)(1),
(2) Date: Jul. 24, 2015

(87) PCT Pub. No.: WO2014/117208
PCT Pub. Date: Aug. 7, 2014

(65) Prior Publication Data
US 2015/0352364 A1 Dec. 10, 2015

Related U.S. Application Data

(60) Provisional application No. 61/758,159, filed on Jan. 29, 2013.

(30) Foreign Application Priority Data
Jan. 29, 2013 (AU) ................................ 2013900265

(51) Int. Cl.
A61N 1/00 (2006.01)
A61N 1/36 (2006.01)
(Continued)

(52) U.S. Cl.
CPC ......... *A61N 1/36128* (2013.01); *A61N 1/0543* (2013.01); *A61N 1/0551* (2013.01);
(Continued)

(58) Field of Classification Search
CPC ............ A61N 1/36128; A61N 1/36046; A61N 1/0551; G06N 3/08
See application file for complete search history.

(56) References Cited

U.S. PATENT DOCUMENTS 4,648,403 A 3/1987 Van Compernolle
7,110,821 B1 9/2006 Ross
(Continued)

OTHER PUBLICATIONS

H.J. Chang et al., "Parameter Optimization in Models of the Olfactory Neural System", Neural Networks, vol. 9, No. 1, 1996, pp. 1-14.
(Continued)

*Primary Examiner* — Robert N Wieland

(57) ABSTRACT

The present disclosure relates to a method for determining stimulation parameters for a neuroprosthetic device performed by a processor of the device. Based on (i) a desired spatial pattern of neural activity, the processor determines stimulation parameters for an array of electrodes of the neuroprosthetic device. The processor determines the stimulation parameters such that a difference between (i) the desired spatial pattern of neural activity and (ii) an estimated spatial pattern of neural activity is optimised. The estimated spatial pattern of neural activity is an estimate of a response of a target neural tissue to being stimulated by the neuroprosthetic device based on the stimulation parameters. This method allows higher resolution stimulation and allows
(Continued)

electrode arrays with higher electrode density to be usefully employed.

20 Claims, 6 Drawing Sheets

(51) Int. Cl.
  *A61N 1/05* (2006.01)
  *G06F 3/01* (2006.01)
(52) U.S. Cl.
  CPC ..... *A61N 1/36046* (2013.01); *A61N 1/36146* (2013.01); *A61N 1/36182* (2013.01); *A61N 1/36185* (2013.01); *G06F 3/015* (2013.01)

(56) References Cited

U.S. PATENT DOCUMENTS

| | | |
|---|---|---|
| 7,860,573 B2 | 12/2010 | Van Den Honert |
| 2007/0067003 A1 | 3/2007 | Sanchez et al. |
| 2009/0312818 A1 | 12/2009 | Horsager et al. |
| 2012/0083861 A1* | 4/2012 | Fried .................. A61N 1/36171 607/76 |
| 2012/0109262 A1 | 5/2012 | Martens |
| 2012/0221075 A1* | 8/2012 | Bentwich ............. A61B 5/0476 607/45 |
| 2012/0296396 A1 | 11/2012 | Moffitt et al. |

OTHER PUBLICATIONS

E.J. Chichilnisky, "A simple white noise analysis of neuronal light response", Institute of Physics Publishing, Network: Computation in Neural Systems, 12, 2001, pp. 199-213.

* cited by examiner

NEUROPROSTHETIC STIMULATION

TECHNICAL FIELD

The present disclosure generally relates to neuroprosthetic stimulation, and more particularly to a method, computer program and controller for determining stimulation parameters for a neuroprosthetic device. In another aspect, there is provided a neuroprosthetic device.

BACKGROUND

Neuroprosthetics refers generally to the use of electrical stimulation to artificially restore lost sensory, cognitive or motor function that might have been damaged as a result of an injury or disease.

SUMMARY

According to a first aspect, there is provided a method for determining stimulation parameters for a neuroprosthetic device, the method comprising:
  based on (i) a desired spatial pattern of neural activity, determining stimulation parameters for an array of electrodes of the neuroprosthetic device such that a difference between (i) the desired spatial pattern of neural activity and (ii) an estimated spatial pattern of neural activity is optimised and the estimated spatial pattern of neural activity is an estimate of a response of a target neural tissue to being stimulated by the neuroprosthetic device based on the stimulation parameters.

The perceived spatial resolution in existing devices is often limited by the widespread response of the neural tissue when it is stimulated by a single electrode. The response to being stimulated by the single electrode overlaps with the response to being simulated by neighbouring electrodes leading to broad, overlapping neural activation profiles from each electrode. Since the method optimises the difference between the desired spatial pattern and an estimated pattern, it is possible to incorporate the diffuse characteristic of the response into the stimulation parameters.

Further, the desired spatial pattern and the estimated spatial pattern are both patterns of neural activity as opposed to mere stimulation patterns, such as electrode potential or current densities. As a result, effects that are due to the properties of the target neural tissue can be incorporated, such as anisotropic effects based on the cell structure of the neurons. Therefore, the resulting perception by a vision impaired user is more similar to what a non-impaired user would see compared to methods that consider only electrical quantities, such as current density or potential.

This leads to higher resolution stimulation and allows electrode arrays with higher electrode density to be usefully employed. Furthermore, in at least one embodiment, the method provides better approximations to the response to natural stimuli, for example, as might be induced by light stimulation in the visual system or acoustic stimulation in the auditory system. This is because the spatial pattern of neural activity, that is, the response of the target neural tissue to being stimulated, can be optimally matched to a spatial pattern of neural activity that would be evoked by a naturally occurring stimulus.

The desired spatial pattern and the estimated spatial pattern of neural activity cover the entire area of interest. As a result, the optimisation of the difference between the desired and the estimated spatial patterns is a global optimisation that incorporates the response evoked by all stimulation electrodes simultaneously. Therefore, the method results in clearer perception and has broader applicability, which is an advantage over methods that are limited to local optimisation, such as limited to current flow between two neighbouring electrodes. These approaches using local optimisation lead to disappointing outcomes in which resolution is not improved or perception is unpredictable.

Determining the stimulation parameters may comprise optimising a non-linear objective function to optimise the difference between (i) the desired spatial pattern of neural activity and (ii) the estimated spatial pattern of neural activity.

In one example, optimising the objective function may comprise minimising error or mean squared error in a measure of neural activity associated with the difference between (i) the desired spatial pattern of neural activity and (ii) the estimated spatial pattern of neural activity.

In another example, optimising the objective function may comprise maximising a likelihood function of (ii) the estimated spatial pattern of neural activity substantially matching with (i) the desired spatial pattern of neural activity.

The stimulation parameters may be determined subject to one or more constraints including one or more of:
  a threshold relating to voltage compliance is not exceeded;
  a threshold relating to charge per phase and/or charge density is not exceeded;
  a threshold relating to power limits is not exceeded;
  a threshold relating to current amplitude is not exceeded;
  a threshold relating to pulse duration is not exceeded;
  a threshold relating to inter-phase gap is not exceeded; and
  axons of passage in the target neural tissue not stimulated.

Determining the stimulation parameters may further comprise estimating the response of the target neural tissue to being stimulated by the neuroprosthetic device based on the stimulation parameters using a linear-non-linear model.

The response of the target neural tissue to being stimulated by the neuroprosthetic device based on the stimulation parameters may be estimated using the linear-non-linear model by performing:
  a linear step, in which a spatio-temporal function is determined as a linear function of the stimulation parameters; and
  a non-linear step, in which using spatio-temporal pattern of neural activity is determined using the result of the linear step by passing the linear spatio-temporal function through a static non-linearity.

In one example, the response of the target neural tissue to being stimulated by the neuroprosthetic device based on the stimulation parameters may be estimated using values of membrane potential of neurons of the target neural tissue given the stimulation parameters.

In this case, the values of membrane potential may be pre-calculated using basis functions of membrane potential, each basis function being defined such that each of its constituent functions represents the membrane potential in the target neural tissue when a single electrode is active with a standard current and the remaining electrodes with zero net current through them.

The values of membrane potential may be pre-calculated based on values of extracellular potential in the vicinity of the target neural tissue given the stimulation parameters. The values of extracellular potential may be pre-calculated using basis functions of extracellular potential, each basis function being defined such that each of its constituent function represents the extracellular potential in the vicinity of the target neural tissue when a single electrode is active with a standard current and the remaining electrodes with zero net current through them.

In one example, the values of membrane potential and/or extracellular potential are calculated using a volume conductor model defined by a partial differential equation in space and one or more boundary conditions. In another example, the values of membrane potential and/or extracellular potential are calculated using a bidomain model of electrical flow.

The stimulation parameters for the array of electrodes may be amplitudes of current pulses applicable by the array of electrodes on the target neural tissue.

The stimulation applied by the array of electrodes may be synchronised using identical rectangular wave, charge-balanced biphasic waveforms. Using rectangular-wave, charged balanced biphasic waveforms, it is relatively easy to build circuitry that achieves charge balance by employing matched constant current sources on each phase of the stimulation parameters.

The estimated spatial pattern of neural activity may represent a mean spike count, averaged over a population of neurons in the vicinity of a spatial variable associated with the target neural tissue.

The stimulation parameters may be determined in real time to dynamically adjust the stimulation parameters according to the target spatial pattern of neural activity. As such, the method allows faster estimation of spatial pattern of neural activity under electrical stimulation According to a second aspect, there is provided a computer program comprising machine-readable instructions for performing the method for determining stimulation parameters for a neuroprosthetic device according to any preceding claim.

According to a third aspect, there is provided a controller for determining stimulation parameters for a neuroprosthetic device, the controller comprising a processor to:
  based on (i) a desired spatial pattern of neural activity, determine stimulation parameters for an array of electrodes of the neuroprosthetic device such that the difference between (i) the desired spatial pattern of neural activity and (ii) an estimated spatial pattern of neural activity is optimised and the estimated spatial pattern of neural activity is an estimate of a response of a target neural tissue to being stimulated by the neuroprosthetic device based on the stimulation parameters.

According to a fourth aspect, there is provided a neuroprosthetic device comprising:
  an array of electrodes to deliver electrical stimulation to a target neural tissue of a subject according to a set of stimulation parameters; and
  a controller to determine the set of stimulation parameters, the controller comprising a processor to:
    based on (i) a desired spatial pattern of neural activity, determine stimulation parameters for an array of electrodes of the neuroprosthetic device such that the difference between (i) the desired spatial pattern of neural activity and (ii) an estimated spatial pattern of neural activity is optimised and the estimated spatial pattern of neural activity is an estimate of a response of the target neural tissue to being stimulated by the neuroprosthetic device based on the stimulation parameters.

BRIEF DESCRIPTION OF DRAWINGS

By way of non-limiting examples, neuroprosthetic stimulation will be described with reference to the following drawings, in which:
FIG. 1($b$) is a schematic diagram of an example method for determining stimulation parameters for the neuroprosthetic device in FIG. 1($a$)

DETAILED DESCRIPTION

Figure 1:
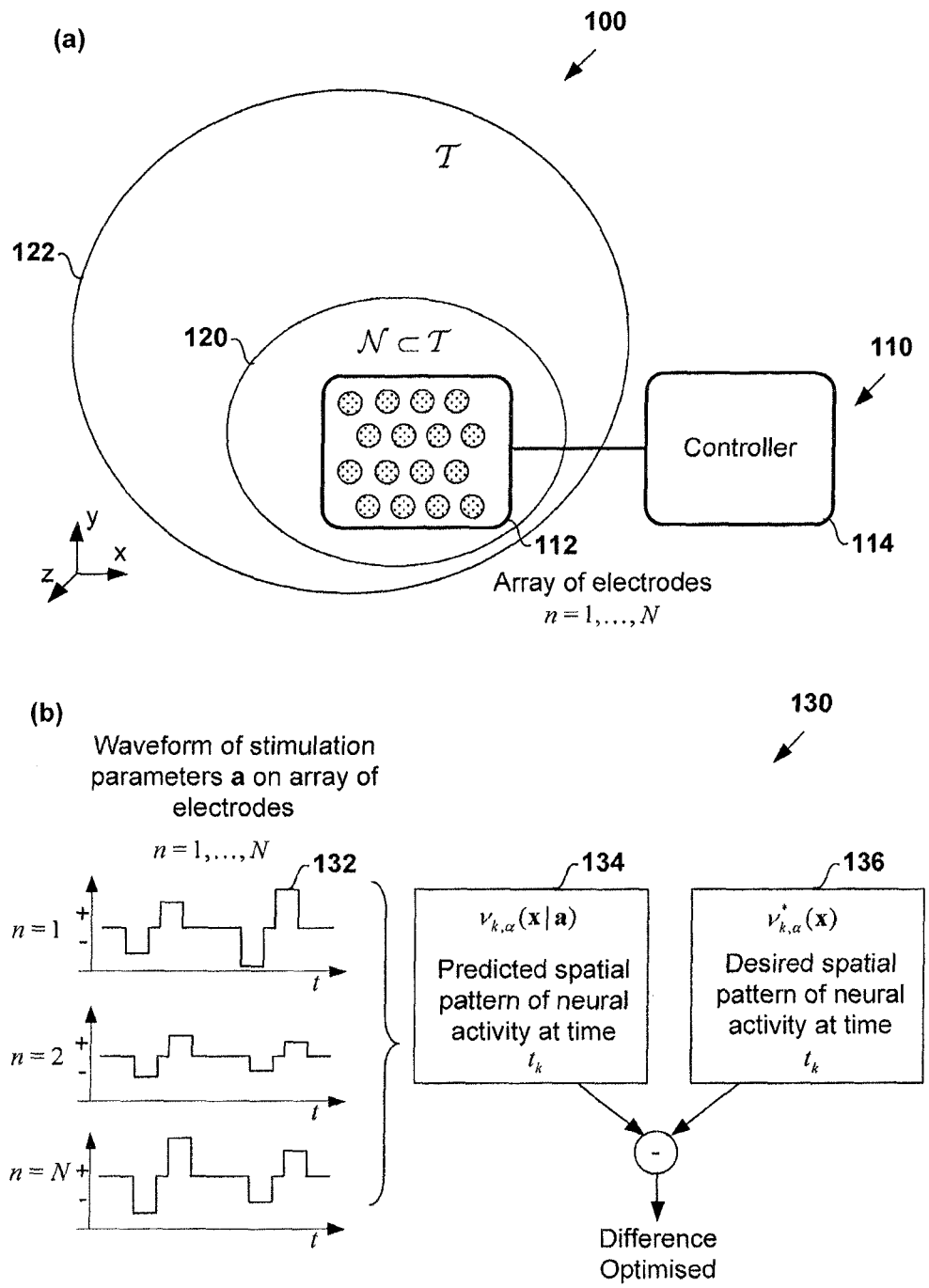
FIG. 1($a$) is a schematic diagram of an example model for neuroprosthetic stimulation using a neuroprosthetic device.

FIG. 1($a$) is a schematic diagram of a model 100 for neuroprosthetic stimulation, which includes an example neuroprosthetic device 110 for delivering electrical stimulation to some neural tissue which is the target of electrical stimulation ("target neural tissue"). The target neural tissue occupies a volume $N \subset T$ which is a subset of the volume of a piece of tissue in three dimensional space T.

The example neuroprosthetic device 110 includes:
  An array of electrodes 112, n=1, . . . , N, to deliver electrical stimulation to a target neural tissue 120, such as using current pulses of various amplitudes that pass through the target neural tissue 120. The geometry of the array of electrodes is defined by the spatial subset occupied by each electrode $E_n \subset T$, $E = \cup_n E_n$.
  A controller 114 that processes information to determine stimulation parameters for the array of electrodes 112.

The neuroprosthetic device 110 may be used to artificially restore function to individuals with neurological impairment such as to restore sensory, cognitive or motor functions. For example, sensory prosthetics may be visual prostheses, auditory prostheses or prostheses for pain relief. Cognitive prostheses may have applications in, for example, brain injury, Parkinson's disease, paralysis, spinal cord injuries, etc.

FIG. 1($b$) is a schematic representation of an example method 130 for determining stimulation parameters $a=(a_1, \ldots, a_N)$ for the array of electrodes 112. The method is performed by the controller 114 before the stimulation parameters are delivered or applied to the array of electrodes 112.

In one example, stimulation is applied via current that passes from each electrode to surrounding neurons in the target neural tissue 120. Synchronised stimulation of the array of electrodes 112 may be used, in which electrodes are stimulated with identical rectangular, charge-balanced biphasic waveforms and current amplitudes a.

As shown at 132 in FIG. 1($b$), each pulse generally has cathodal (−) and anodal (+) components defined by current amplitudes and durations that result in an overall zero net charge (i.e. charge balance) for the pulse. This class of synchronised stimuli is broad enough to allow considerable scope for the spatial shaping of neural activity. In this example, each waveform 132 is a train of isolated biphasic pulses, with an interphase gap and different amplitudes for each pulse. Note that the waveform 132 in FIG. 1(b) is merely an example, and may have an opposite phase in other applications. Rectangular, charged balanced biphasic waveforms are used because these are the standard waveforms employed by nearly all neuroprosthetic devices. This is because it is comparatively easy to build circuitry that achieves charge balance by employing matched constant current sources on each phase of the stimulus.

Asynchronous stimulation and stimulation with different waveforms, such triphasic waveforms, on different electrodes may also be used, but they generally give rise to highly complicated patterns of current flow between electrodes (that would change each time the ratio of currents flowing through the electrodes changed). This degree of complication is probably unnecessary for the spatial shaping of neural activity and is likely to present problems for achieving charge balance on each electrode.

The electrical stimulation by the array of electrodes 120 evokes a spatial pattern of neural activity in the target neural tissue 120. A spatial pattern or map of neural activity may be described using non-negative real numbers: $v_{k,a}(x)$, which are functions of a spatial variable x, a post-stimulus time period k (i.e. $t_k$) and possibly the type of neuron being described α. Each neuron type α may respond differently to a given electrical stimulus, due to its different size, shape or electrical properties.

Any suitable measure of neural activity may be used. For example, $v_{k,a}$ (x) may be interpreted as a mean spike-count, averaged over a population of neurons in the vicinity of x, for some time following $t_k$ for neurons of type α. It could also be interpreted as the spike-rate of a single neuron or the probability of spiking for a single neuron. The post-stimulus time period may be some period between $t_k$ and $t_{k+1}$, usually, but not always, this entire period.

Other suitable neural activity measures include one or more of the following, or any values derived from them: evoked potential; local field potential; multi-unit or single-unit activity; electroencelphalogram; neural information; neural information rate; membrane potential; neural firing; compound action potential; electroretinogram; and auditory brainstem response.

As shown in FIG. 1(b), the controller 114 determines stimulation parameters a=($a_1$, . . . , $a_N$) to shape the spatial pattern of neural activity electrically evoked in the target neural tissue 120. The phrases "shape the spatial pattern" and "spatial shaping" here refer generally to any suitable techniques for forming the spatial pattern of neural activity electrically evoked by the stimulation parameters. For example, conventional forms of current steering, such as current focusing and steering, may be used. Current focussing and steering is discussed in Bonham, Ben H.; Litvak, Leonid M., "Current focusing and steering: Modeling, physiology, and psychophysics", Hearing Research vol. 242 issue 1-2, the content of which is incorporated here by reference.

The stimulation parameters are determined for the array of electrodes 120 such that the difference between the following is optimised:
(i) target or desired spatial pattern of neural activity (see 136), denoted by $v_{k,a}*(x)$.

(ii) estimated spatial pattern of neural activity, which is an estimate of the response of the target neural tissue 120 to being electrically stimulated by the array of electrodes 112 of the neuroprosthetic device 110 based on the stimulation parameters a (see 134), denoted by $v_{k,a}(x|a)$.

It should be understood that the optimisation process involves optimising the "difference" between (i) and (ii) directly or indirectly. An objective function representing the difference, or representing any other metrics associated with the difference, may be used in the optimisation process. In effect, the difference is optimised; i.e., the (ii) estimated spatial pattern of neural activity evoked by the stimulation parameters optimally matches with the (i) target or desired spatial pattern of neural activity.

For example, other possible metrics associated with the difference are as follows:
(1) the Kullback-Leibler divergence when the spatial pattern of neural activity is described by a probability function.
(2) metrics for computing the difference between spike trains when the spatial pattern of neural activity is described by a set of spike trains. Example of such metrics are described in the following two papers, which are herein incorporated by reference:
a) Victor, J D and Purpura K P, "Metric-space analysis of spike trains: theory, algorithms and application", Network 8, 127-164 (1997), and
b) van Rossum, M C W, "A novel spike distance", Neural Computation, 13, 751-763 (2001).

Once the stimulation parameters a are determined, they may be applied to the target neural tissue 120 using the array of electrodes to evoke a spatial pattern of neural activity that approximates the target spatial pattern. The stimulation parameters may be determined in real time to dynamically adjust the stimulation parameters according to the target spatial pattern of neural activity.

The example method involves global optimisation of stimulation parameters for direct shaping of neural activity evoked in the target neural tissue according to the stimulation parameters a. Advantageously, spatial resolution of the neuroprosthetic device 110 is improved, since more predictable evoked spatial pattern of neural activity may be determined. Furthermore, as will be explained in more detail below, the method may be implemented using fast and accurate models with pre-calculated values that facilitate real-time determination of stimulation parameters.

Determination of Stimulation Parameters 200

Figure 2:
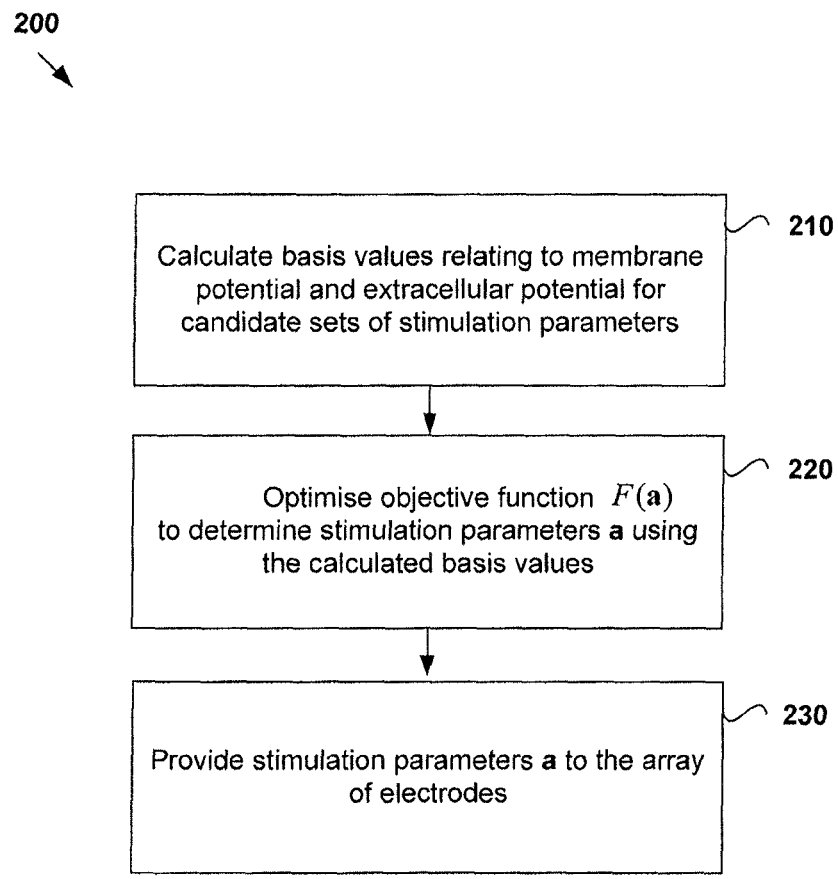
FIG. 2 is a flowchart of an example method for determining stimulation parameters by optimising an objective function.

FIG. 2 is a flowchart of an example method 200 for determining the stimulation parameters in the form of current amplitudes a by solving an optimisation problem.

At block 210, values relating to membrane potential and extracellular potential in the vicinity of x at the target neural tissue 120 are pre-calculated for various candidate sets of stimulation parameters. The purpose is to facilitate fast estimation of (ii) spatial pattern of neural activity electrically evoked by a given candidate set of stimulation parameters.

At block 220, an objective function F(a) is optimised to determine a set of stimulation parameters, a, using the values pre-calculated at block 210. The objective function F(a) may be optimised subject to one or more constraints.

The set of stimulation parameters a for the array of electrodes 112 is determined such that the difference between the following is optimised (i.e. positive difference minimised or negative difference maximised):

(i) a desired spatial pattern of neural activity; and
(ii) an estimated spatial pattern of neural activity, which is the response of the neural tissue to being electrically stimulated by the neuroprosthetic device based on the set of stimulation parameters a.

Stopping criteria may be employed in the optimisation algorithm, depending on the objective function F(a). In this case, one or more stopping criteria are checked to determine whether the objective function has been optimised. If not optimised, block 220 is repeated until stimulation parameters a that optimise the objective function are determined. Otherwise, if optimised, block 230 is performed.

At block 230, the determined stimulation parameters a are used by the array of electrodes 112 to deliver stimulation to the target neural tissue 120.

Any suitable objective function may be used. The objective function is designed such that, when optimised, the estimated spatial pattern of neural activity approximately matches with the desired spatial pattern of neural activity. Blocks 210 to 230 will be explained in more detail as follows.

Although current amplitudes have been used as stimulation parameters here, it will be appreciated that, depending on the applications, other stimulation parameters, such as pulse width, charge per phase, inter-pulse gap, or values derived from them, may be used.

Pre-Calculation of Potential Values 210

At block 210, various values required for fast estimation of spatial pattern of neural activity electrically evoked by a set of stimulation parameters are pre-calculated by the controller 114.

Underlying the operation of spatially shaping neural activity is a model of how electrical stimulation evokes a spatial pattern of neural activity. In general, a linear-non-linear model may be used to estimate the spatial pattern of neural activity evoked by the stimulation parameters. The linear-non-linear model involves the following steps:
(1) a linear step, in which a spatio-temporal function is determined as a linear function of the stimulation parameters; and
(2) a non-linear step, in which using spatio-temporal pattern of neural activity is determined using the result of the linear step by passing the linear spatio-temporal function through a static non-linearity.

In one example, a volume conductor model may be used, which involves two stages:
(1) The first stage is a volume conductor model, which involves modelling the electrical potential and current density in the target tissue at a macroscopic scale due to the array of electrodes 112. As will be explained further below, the volume conductor model is used to calculate fundamental basis $\{V_{e_f,n}(x,t)\}$ and current basis $\{V_{e_g,n}(x,t)\}$ for the extracellular potential in the vicinity of x in the target neural tissue.
(2) The second stage is a local model of neural activation, which uses the local extracellular electrical potential or current density in the vicinity of neurons to estimate the evoked neural activity. As will be explained further below, the local model is used to calculate current bases for the longitudinal and transverse modes of the membrane potential $\{V_{m_a,n}^P(x,t)\}$ and $\{V_{m_a,n}^\perp(x,t)\}$. From this, an aggregate membrane potential is calculated for a particular set of stimulation parameters. Finally, the membrane potential is converted in to a measure of spiking activity by applying a non-linear function.

Although a volume conductor model is used here as an example, other suitable linear-non-linear models such as a bidomain model may be used. A bidomain model is a model of electrical current flow in tissue in which electrically conductive continua representing the intracellular and extracellular spaces are coupled at all points in space by equations representing the dynamics of a cellular membrane. Values of membrane potential and/or extracellular potential may be calculated using the bidomain model.

Figure 3:
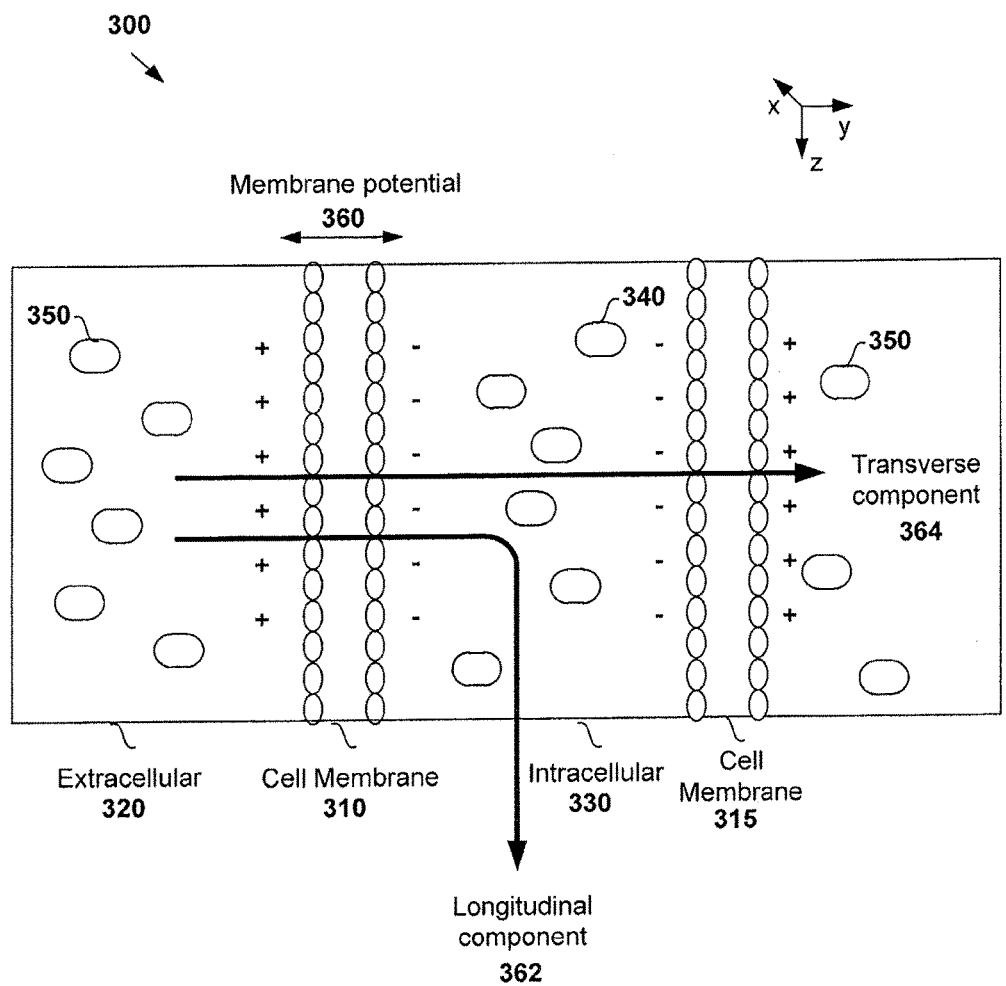
FIG. 3 is a schematic diagram illustrating a cell membrane, extracellular potential and membrane potential of a neuron.

Neural tissue contains two distinct cell types: neurons, or nerve cells, responsible for the transfer and processing of information in the nervous system, and neuroglia or supporting cells that isolate the neurons. The relationship between extracellular potential and membrane potential of a neuron or nerve cell is shown in the diagram 300 in FIG. 3.

Membrane potential is the difference in electrical potential between the interior (intracellular 330) and the exterior (extracellular 320) of the neuron or nerve cell. The membrane potential is due to the differences in concentration of ions 340, 350 on opposite sides of the cell membrane 310. The longitudinal component 362 of the membrane potential is generally parallel to the length of the (elongated) cell membrane, and the transverse component 364 generally transverse to the length of the cell membrane.

There are a number of types of neurons: sensory neurons that respond to sensory stimuli (touch, sound, light, etc.), and motor neurons that receive signals from the brain and spinal cord. A representative neuron generally has four parts:
(1) cell body or soma with a perikaryon, region around the nucleus;
(2) dendrites, branch from the soma containing post-synaptic receptors;
(3) axon, elongated process attached to the soma along which action potentials are sent; and
(4) synaptic terminals, ends of the axon that communicates with other cells.

Figure 4:
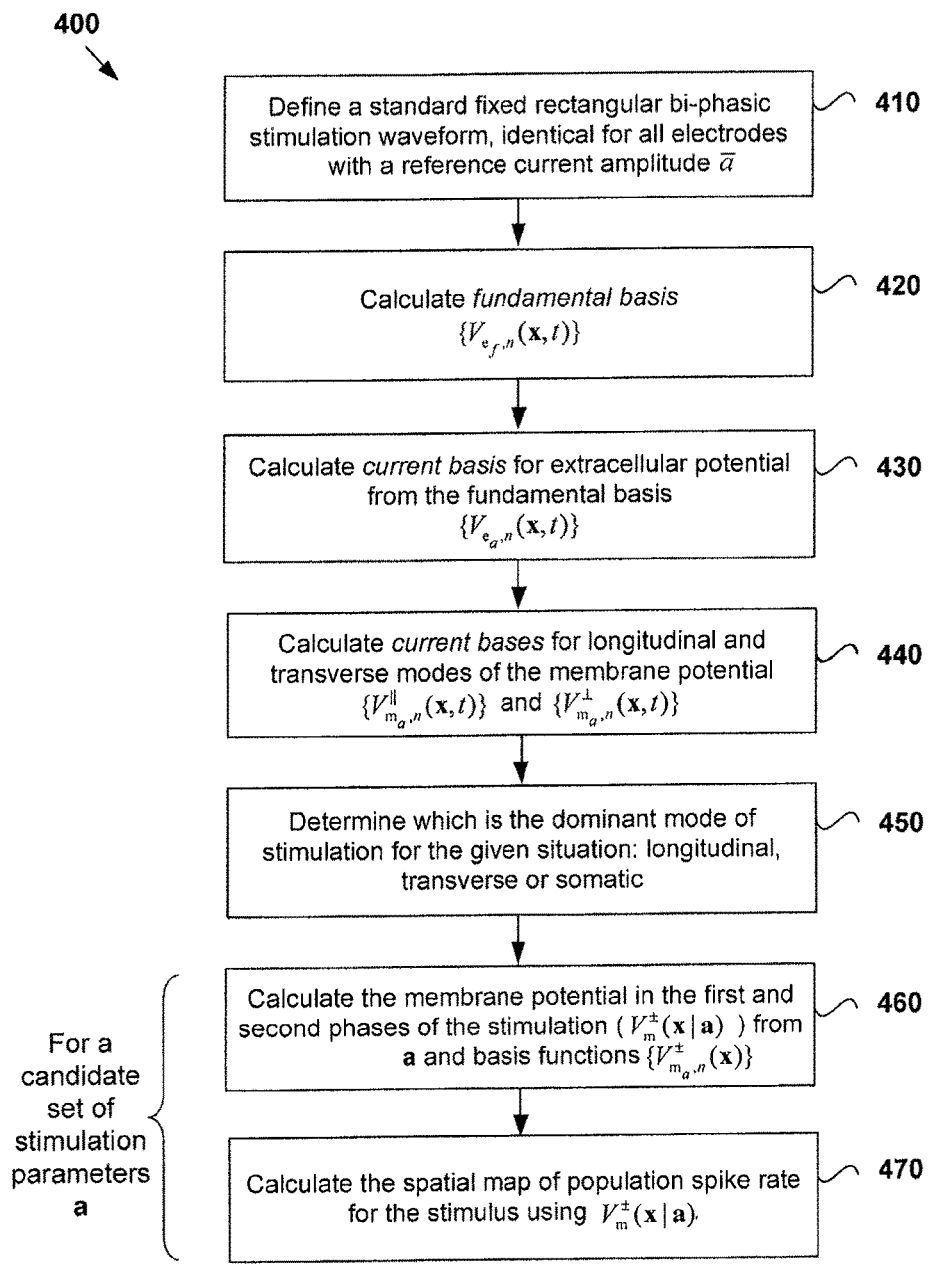
FIG. 4 is a flowchart of an example method for determining values required for determining the stimulation parameters in FIG. 2 in real time.

In one example implementation shown in the flowchart 400 in FIG. 4, block 210 in FIG. 2 further includes the following.

At block 410, determine a standard fixed rectangular bi-phasic stimulation waveform, identical for all electrodes 112 with a reference current amplitude $\bar{a}$. This is used in all following calculations.

At block 420, calculate fundamental basis $\{V_{e_f,n}(x,t)\}$ for the extracellular potential using the governing partial differential equation (PDE) for the volume conductor model (see Eqs. (2) and (3) below), together with the boundary conditions (see Eqs. (7), (9) and (10) below). The specific boundary conditions on the array of electrodes 112 for the fundamental basis is defined in Eq. (11) below, together with the general electrode boundary condition in Eq. (7) below.

At block 430, calculate current basis $\{V_{e_g,n}(x,t)\}$ for the extracellular potential from the fundamental basis using Eq. (15) and (16) below.

At block 440, calculate current bases for the longitudinal and transverse modes of the membrane potential $\{V_{m_a,n}^P(x,t)\}$ and $\{V_{m_a,n}^\perp(x,t)\}$ using Eqs. (18) and (20) below, respectively, with driving terms given by the current basis functions for the extracellular potentials as described by Eqs. (22) and (23) below.

At block 450, determine the dominant mode of stimulation for the given situation: longitudinal, transverse or somatic. In general, the dominant mode has the largest magnitude. If multiple modes have comparable magnitudes, both modes should be included. For the dominant mode, determine sampling times $t^+$ and $t^-$ for the maximum amplitude of polarisation of the membrane potential basis functions $\{V_{m_a,n}(x,t)\}$ during the first and second phase of the bi-phasic stimulation waveform. Basis functions for the membrane potential at these times, $\{V_{m_a,n}^{\pm}(x)\}$, are then calculated.

The following are performed for each candidate set of stimulation parameters a.

At block 460, calculate membrane potential in the first and second phases of the stimulation ($V_m^{\pm}(x|a)$) from the candidate set of stimulation parameters a and respective basis function $\{V_{m_a,n}^{\pm}(x)\}$ for the longitudinal mode (using Eq. (24) below), or for the transverse mode (using Eq. (25) below).

At block 470, estimate the spatial pattern of neural activity for the candidate set of stimulation parameters. For example, the estimated spatial pattern may be calculated using $V_m^{\pm}(x|a)$ in Eq. (28) below for mean spike rate, or Eq. (27) below for spike probability and Eq. (29) below for the variance in the spike rate.

The above will be explained in more detail with reference to the volume conductor model and local neural activation model below. As previously mentioned, other suitable models such as a bidomain model may be used instead.

Volume Conductor Model

The volume conductor model models the electrical potential and current density in the target neural tissue due to the array of electrodes 112 at a macroscopic scale. The set of equations defining the volume conductor model are given by the governing partial differential equation, Eqs. (2) and (3) together with the boundary conditions Eqs. (7), (9) and (10) below.

The extracellular electrical potential in the tissue, $V_e$, occupying the space, T, is predicted using the volume conductor model. This comprises a linear partial differential equation (PDE) in space and possibly time, together with a set of boundary conditions that together determine the potential. One description uses the Laplace-type equation:

$$\nabla \cdot \sigma_e(x) \nabla V_e(x,t|a) = 0 \quad x \in T \backslash E \quad (1)$$

where $\sigma_e(x)$ is the aggregate extracellular tissue conductivity. It describes the mean conductivity to current flow in the extracellular domain in a small piece of tissue, taking into account the confined extracellular space between neighboring cells and the possibly tortuous paths taken by current through the extracellular space.

In general, the conductivity is inhomogeneous whenever the tissue comprises different types or subtypes of tissue as these typically have different electrical properties. This means that $\sigma_e$ is a non-trivial function of x. Neural tissue is also typically electrically anisotropic because the cellular structure is different along different directions (e.g. a nerve fibre bundle has distinct directions parallel and perpendicular to the fibre axis). In this case, $\sigma_e$ varies as a function of direction and is described as a three-dimensional square matrix with each dimension corresponding to a spatial dimension.

According to the example in Eq. (1), it is assumed that the tissue is a simple Ohmic conductor so that the local current density is related to the local electric field by Ohm's law. More generally, the conductivity of neural tissue can be a function of the temporal and spatial frequencies of the electric potential, in which case Eq. (1) can be generalised to a more complicated form:

$$\nabla \cdot J_e(x,t|a) = 0 \quad (2)$$

$$J_e(x,t|a) = s_e * \nabla V_e(x,t|a) \quad x \in T \backslash E \quad (3)$$

where $s_e(x, t)$ is the conductivity tensor and * denotes convolution in space and time.

The effect of electrical stimulation is typically described using boundary conditions on the electrodes, $E_n$. There are a variety of models for specifying the way that current flows out of an electrode, which differ in their treatment of the electrode/electolyte interface. They give rise to different spatio-temporal distributions of current density across the surface of the electrodes, which can affect the pattern of neural activation for neurons that are close to the surface of the electrode.

Three example models for the electrode/electrolyte interface are described below, but it should be understood that other models may be used.

(a) The simplest model assumes that there is a constant current density on the surface of each electrode:

$$J_e(x,t|a) \cdot \hat{n} = \frac{a_n(t)}{|\partial E_n|} \quad \forall x \in \partial E_n, \quad (4)$$

where $\hat{n}$ is a unit normal to the electrode surface $\partial E_n$ and $|\partial E_n|$ is the area of that electrode surface.

(b) An alternative model assumes that the electrode is an equipotential surface $$V_e(x,t|a) = v_n(t) \forall x \in \partial E_n, \quad (5)$$

where the unknown equipotential values $v = (v_1, \ldots, v_n)$ are determined by the total current on each electrode. This can be calculated using an approach to be described shortly.

The main difference between these two models is that the equipotential model gives rise to very large electric fields and current densities on the perimeter of the electrode compared to its center, whereas current density is constant across the electrode surface for the current density model by definition. Indeed, the analytical solution for an idealised disc electrode with the equipotential boundary condition predicts that the magnitude of current density on the circumference diverges to infinity. While these two approaches are relatively simple, they may not be particularly accurate.

The electode/electrolyte interface has its own significant impedance due the movement of ions to form a double layer on its surface. A simple and reasonably accurate way to model this is as follows.

(c) A third model considers specific resistance and capacitance in parallel:

$$J_e(x,t|a) \cdot \hat{n} = C_i \frac{dV_{i,n}}{dt} + \frac{V_{i,n}}{R_i} \quad \forall x \in \partial E_n, \quad (6)$$

where $V_{i,n}(x,t) = V_e(x,t) - v_n(t)$ is the interface potential for all $x \in \partial E_n$ and $v_n(t)$ is the potential on the electrode side of the interface which is assumed to be equal across the surface.

It is possible to choose more complicated and realistic impedance models of the electrode/electrolyte interface. The third model is also better able to account for the tendency of current to short circuit through neighboring electrodes rather than pass through tissue. In the electrical impedance tomography (EIT) literature, the model is known as the "complete model". The impendance computed by that complete model has been shown to be withing 1 percent from experimental measurements. In the EIT literature, the constant current density model is known as the gap model.

These three electrode models can be summarised using a single formulation such that the boundary condition on the electrodes is as follows:

$$\alpha J_e(x,t|f)\cdot \bar{n} + \beta V_e(x,t|f) = f_n(t) \forall x \in \partial E_n, \quad (7)$$

where $f=(f_1, \ldots, f_N)$ is the fundamental variable driving the electrode: $f_n = a_n/|\partial E_n|$ or $v_n$ corresponding to boundary conditions on the electrode for constant current density in the first case and equipotentiality or complex impedance across the electrode-electrolyte interface in the second case.

There is also often a distant return electrode, which is set to a particular potential, often the ground or voltage supply of the stimulator. Consequently, this serves as a voltage reference in the model. In the context of current steering, this electrode can be used to source or sink any residual current from the stimulating electrodes so that $$a_0(t) = \sum_{n=1}^{N} a_i(t). \quad (8)$$

It can be assumed that the electrode is sufficiently far from all stimulating electrodes that it can be taken to be at infinity.

In addition to boundary conditions of the electrodes, it is often necessary to stipulate boundary conditions on the remaining surface of the stimulating device. This is usually an insulator. It may also be necessary to define boundary conditions elsewhere, such as on the exterior surface of the tissue, which again is usually insulating $$J_e(x,t|a) = 0 \forall X \in \partial T_J \quad (9)$$

or it could be a ground potential, $$V_e(x,t|a) = 0 \forall x \in \partial T_V. \quad (10)$$

In summary, the set of equations defining the volume conductor model are given by the governing partial differential equation, Eqs. (2) and (3), together with the boundary conditions, Eqs. (7), (9) and (10).

There are two critical aspects of the volume conductor model defined above that allow an arbitrary potential arising from the stimulating array of electrodes 112 to be described by the following set of basis function. First, the PDE and equations describing boundary conditions are linear, in all the variations described. Second, all variations of the boundary coundictions are homogeneous. This means that if all basis functions obey the PDE and the boundary conditions for a particular variation of the model, then arbitrary voltage can be described a weighted sum of these basis function and will also obey the PDE and boundary coundictions.

The three types of boundary condition summarised by Eq. (7) give rise to the following fundamental basis consisting of functions defined by:

$$V_{e_f,n}(x,t) = V_e(x,t|f=\bar{f}_n e_n), \quad (11)$$

where f is the fundamental variable driving the electrode, $\bar{f}_n = \bar{a}/|\partial E_m|$ or $\bar{v}_n$ gives a standard electrode current density, external electrode potential or internal electrode potential. $e_n$ is the N-vector with a 1 in the n th place and zeros elsewhere.

In terms of these basis functions, the general extracellular potential in the tissue may be expressed as:

$$V_e(x,t|f) = \sum_{n=1}^{N} \frac{f_n}{\bar{f}_n} V_{e_f,n}(x,t). \quad (12)$$

The basis functions obey the governing partial differential equation, Eqs. (2) and (3), together with the boundary conditions, Eqs. (7), (9) and (10), and may be calculated by solving these via, for example, finite element methods.

It is generally more convenient to use a basis defined so that each of its constituent functions represents the potential in the tissue when a single electrode is active with standard current $\bar{a}$ and the remaining electrodes are left floating (i.e. zero net current through them). That is, the basis consists of the set of functions:

$$V_{e_a,n}(x,t) = V_e(x,t|a=\bar{a}e_n). \quad (13)$$

The current basis can be derived from the fundamental basis via a basis transform. Defining $J_{e_a,n}(x,t) = -\sigma^* \nabla V_{e_a,n}(x,t)$, the members of the current basis satisfy $$\oiint_{\partial E_n} J_{e_a,n}(x,t) \cdot \bar{n} dS = \bar{a} \delta_{nm}, \quad (14)$$

where $\delta_{nm} = 1$ for n=m and $\delta_{nm} = 0$ for n≠m.

The change of basis is then given by:

$$V_{e_a,n}(x,t) = \sum_{m} [H^{-1}]_{nm} V_{e_f,m}(x,t) \quad (15)$$

$$H_{nm} = \frac{1}{\bar{a}} \oiint_{\partial E_m} J_{e_f,n}(x,t) \cdot \hat{n} dS. \quad (16)$$

$H_{nm}\bar{a}$ is the total current through electrode m for the fundamental basis function $V_{e_f,n}$. Conversely, the fundamental variable driving the electrode (as defined in Eq. (7)) for current basis function $V_{e_a,n}$ on electrode m is $[H^{-1}]_{nm} \bar{f}_n$.

The current basis functions $V_{e_a,n}(x,t)$, are pre-calculated at block 440 in FIG. 4 and used to rapidly calculate the potential in the tissue based on an arbitrary set of stimulation parameters a:

$$V_e(x,t|a) = \sum_{n=1}^{N} \frac{a_n}{\bar{a}} V_{e_a,n}(x,t) \quad (17)$$

Pre-calculation is important for any real time implementation of a current steering algorithm.

Local Model of Neural Activation

The second stage of the model uses knowledge of the extracellular potential or current density in the tissue from the first stage, and uses it to predict the local activation of a population of neurons, $v_{k,a}(x|a)$.

This local model of neural activation must be highly parsimonious for it to be useful for a neural activity shaping algorithm that can run in real time. To this end, a model that uses an activation function is employed. The model is derived from the local potential $V_e(x|a)$ or current density $J_e(x|a)$, which is then passed through a static sigmoidal non-linearity to give the neural activity.

The concept of an activating function was introduced by F. Rattay, "The basic mechanism for the electrical stimulation of the nervous system", Neuroscience, 89(2):335-346, 1999. The content of Rattay's article is herein incorporated by reference. This concept is generalised here to include other modes of electrical excitation of neurons besides the longitudinal mode that was subject of Rattay's original paper. We consider both cylindrical neurites that model activation of the axon, and spherical neurites that model activation of the soma.

For a cylindrical axon, in addition to the longitudinal mode of stimulation, there is also a transverse mode. Using the example in FIG. 3, cell membranes 310, 315 represent membranes of a cylindrical axon. The z-axis is parallel to the direction of the axon, whereas the x-axis is transverse to the direction of the axon. The longitudinal 362 and transverse 364 modes are in the directions of the z-axis and x-axis respectively.

The longitudinal and transverse components of the transmembrane potential, $\overline{V}_m^P(x, t)$ and $\overline{V}_m^\perp(x,t)$, in the subthreshold regime can be related to the extracellular tissue potential via the following equations:

$$\lambda_{0_V}^2 \frac{\partial^2 V_m^P}{\partial z^2} - \tau_m \frac{\partial V_m^P}{\partial t} - V_m^P = -\lambda_{0_V}^2 \frac{\partial^2 V_e}{\partial z^2}, \qquad (18)$$

where $$\lambda_{0_V}^2 = \frac{R_m}{2\pi a r_i} = \frac{r_m}{r_i}. \qquad (19)$$

$$\tau^\perp \frac{d\overline{V}_m^\perp}{dt} + \overline{V}_m = -R\left(\frac{\partial \overline{V}_e}{\partial x} - j\frac{\partial \overline{V}_e}{\partial y}\right). \qquad (20)$$

The time constant governing the above equation is:

$$\tau^\perp = \left(\frac{1}{R_m} + \frac{n}{\rho_i a + n\rho_e d}\right)^{-1} C_m \qquad (21)$$

The longitudinal mode is described using a cable equation. The other is a PDE discussed in the following articles, the content of which are herein incorporated by reference: H. Meffin, Tahayori, B., Grayden, D. B, Burkitt, A. N., "Modeling extracellular electrical stimulation: I. Derivation and interpretation of neurite equations", Journal of Neural Engineering, vol. 9, p. 065005, 2012; and B. Tahayori, Meffin, H., Dokos, S., Burkitt, A. N., Grayden, D. B., "Modeling extracellular electrical stimulation: II. Computational validation and numerical results", Journal of Neural Engineering, vol. 9, p. 065006, 2012.

Basis functions for the longitudinal and transverse modes of the membrane potential can then be defined, which can be pre-calculated at block 440 in FIG. 4 and used to directly calculate the membrane potential for any set of stimulation currents a. They are solutions to Eqs. (18) and (20), respectively, with:

$$V_{m_a,n}^P : V_e = V_{e_a,n} \text{ in Eq. (13)} \qquad (22)$$

$$V_{m_a,n}^\perp : \overline{V}_e = \overline{V}_{e_a,n}, \text{ in Eq. (13).} \qquad (23)$$

Then, the longitudinal or transverse components of the membrane potential may be expressed in terms of these basis functions as:

$$V_m^P(x, t \mid a) = \sum_{n=1}^N \frac{a_n}{\overline{a}} V_{m_a,n}^P(x, t) \qquad (24)$$

-continued $$\overline{V}_m^\perp(x, t \mid a) = \sum_{n=1}^N \frac{a_n}{\overline{a}} \overline{V}_{m_a,n}^\perp(x, t). \qquad (25)$$

An example basis function for $V_{m_a,n}^P$ for a square electrode is shown in FIG. 5(d). Fibre orientation is parallel to the y-axis. The electrode is 20 μm from the retinal surface, and has sides of length 120 μm.

A limitation of the above approach is that it ignores the effects of micro-scale cellular geometry on the electrical potential and current flow. Such effects include the connection of the axon to the soma, the branching of dendrites, non-cylindrical dendrites or non-spherical somas and the effects of the particular micro-scale geometry of neighbouring cells.

Self Consistency of Volume Conductor and Local Neural Activation Models

The model transforms the linear (subthreshold) membrane potential $V_m(t)$ into a probability of spiking. There are several issue to contend with here.

(1) The first issue is that electrical stimulation of neurons may occur either via direct depolarisation of the neurite via the local electrical potential, or indirectly via stimulation of other neurons that are presynaptic to the neuron under consideration. Although direct stimulation has been considered here, it will be appreciated that indirect stimulation may also be employed. In the retina, thresholds for direct stimulation are typically lower than those for indirect stimulation by a factor of 2 to 3

(2) The second issue is that $V_m$ is a function of distance along the axon. If $V_m$ becomes suprathreshold at any point along the axon then a spike will result. Thus, neurons with somas that are remote from the electrode, but whose axons pass in the vicinity of the electrode, can be stimulated. This is generally undesirable as it leads to excitation of neurons that are not local to the electrode and result in a loss of spatial resolution in stimulation. However, the lowest thresholds for stimulation of the neuron occur at the sodium channel band in the axon initial segment about 20 μm to 50 μm from the soma. The threshold for the Na channel band is typically around a factor of two smaller than the threshold for stimulation of axons of passage. The consequence of this is that, in order to achieve local excitation of neurons, the membrane potential should be great than the threshold for the Na channel band but less than the threshold of axons of passage; i.e., $$V_{AIS} \leq V_m \leq V_{AOP}. \qquad (26)$$

(3) The third issue is that for the transverse mode of stimulation, $V_m$ is a function of the angular coordinate around the cylindrical axon. Similarly, for somatic stimulation, $V_m$ is a function of angular position around a spherical soma. We assume that the probability of a spike related to the maximal depolarisation as a function of these angular coordinates. As a result, $V_m$ is related to the magnitude of the extracellular electric field in the plane transverse to the axon.

(4) The fourth issue is that $V_m$ is a function of time following the initiation of the pulse. This will depend primarily on the pulse waveform, but also other aspects such as the electrode-electrolyte interface, the temporal filtering properties of the tissue and the temporal filtering properties of the neurite being stimulated. Potentially, this can lead to quite complicated waveforms for the linear response of the membrane potential. These different waveforms interact with the non-linear dynamics of the voltage gated ion channel of neurons, especially the Na channels associated with spike initiation.

To simplify this complicated situation and make it mathematically tractable, it is assumed that, for any given biphasic stimulus waveform, the probability of spiking depends on the value of $V_m$ the end of the first phase of stimulation.

(5) The fifth issue is that spiking in response to electrical stimulation occurs stochastically, not deterministically. Typically, direct stimulation of an axon results in a maximum of one spike. Empirically, for a single electrode, the probability of this spike occurring for a given stimulus waveform is related to the driving current in the electrode by a sigmoidal non-linearity, which typically saturates at a probability of 1 at high stimulus current and is 0 at low levels of stimulus current. For a single electrode and given waveform, $V_m$ is proportional to the driving current. Consequently, spike probability is modelled via a sigmoidal non-linearity that is specific to each waveform:

$$p(x|a) = g_c(V_m|a). \quad (27)$$

Here, c denotes that the sigmoidal function $g_c$ depend on the particular stimulus configuration; i.e., it depends on factors such as the stimulus waveform, the mode of stimulation (longitudinal, transverse, or somatic), the type of neuron, and whether stimulation is via the axon initial segment or via an axon of passage.

(6) A sixth issue is the role of stimulus history in the probability of spiking as a result of the present stimulus. Here, we assume that stimulation occurs at a sufficiently low rate that the probability of spiking is independent of the previous stimulus history. In the retina, the effect of previous stimulus history on direct stimulation appears to be minimal.

For the purposes of optimising perception due to electrical stimulation, it is necessary to control the response of an ensemble of neurons rather than an individual neuron. It is assumed that such ensembles are distinguished according to the type of neuron involved and their spatial position x, which is assumed to be approximately the same for all neurons in the ensemble. The population response to an electrical stimulus can be described by the fraction of neurons in the population that respond with a spike, v. Assuming the neurons respond to the electrical stimulus independently, then for sufficiently large numbers of neurons in the ensemble the response probability is Gaussian with mean and variance:

$$\bar{v} = g_c(V_m|a) \quad (28)$$

$$\Delta_v^2 = g_c(V_m|a)(1 - g_c(V_c|a))/N \quad (29)$$

Within any such ensemble, variation in neural parameters will result in a distribution of response probabilities to a given electrical stimulus.

Optimisation 220

Referring to block 220 in FIG. 2 again, an objective function, F(a), is solved to determine a set of stimulation parameters a using the values pre-calculated at block 210. The objective function, F(a), may be solved subject to one or more constraints.

The set of stimulation parameters a for the array of electrodes 112 is determined such that the difference between the following is optimised (such as minising the absolute value of the difference, maximising the negative absolute value of the difference, or other equivalent formulations of the optimisation):

(i) a target spatial pattern of neural activity; and (ii) an estimated spatial pattern of neural activity, which is an estimate of the response of the target neural tissue 120 to being electrically stimulated by the array of electrodes 112 of the neuroprosthetic device 110 based on the set of stimulation parameters a.

In one implementation, the objective function may be a function of mean squared error in the mean population spike rate $\bar{v}(x|a)$:

$$F_{\bar{v}}(a) = \frac{1}{|N|} \int_N dx (v(x|a) - v^*(x))^2, \quad (30)$$

where
N is the portion of tissue over which the optimisation is occurring,
|N| is the volume of that portion,
v(x|a) is the estimated spatial pattern of neural activity given parameters a, and
v*(x) is the target spatial pattern of neural activity.

The objective function, $F_{\bar{v}}(a)$, may be subjected to one or more constraints relating to some safety and efficacy constraints, such as but not limited to:
current levels do not exceed threshold(s) relating to voltage compliance;
safety limits or thresholds relating to charge per phase and/or charge density are not exceeded;
a threshold relating to power limits is not exceeded;
a threshold relating to current amplitude is not exceeded;
a threshold relating to pulse duration is not exceeded;
a threshold relating to inter-phase gap is not exceeded; and
axons of passage in the target neural tissue not stimulated.

The first two constraints can be described in terms of a limit on stimulation parameters (e.g. currents):

$$|a_i| < a_{max,i}. \quad (31)$$

The third constraint may be interpreted as desiring a sufficiently small probability of stimulating axons of passage:

$$\bar{v}_{AP}(x|a) < \delta \forall x \in N. \quad (32)$$

The third constraint is non-linear in a and is quite difficult to handle. In one implementation, the third constraint may be treated as a 'soft constraint' by incorporating it into a revised objective function:

$$F_{\bar{v},AP}(a) = \frac{1}{|N|} \int_N dx (\bar{v}(x|a) - \bar{v}^*(x))^2 + (\bar{v}_{AP}(x|a))^2. \quad (33)$$

Although one example objective function is provided above, it should be understood that other suitable objective functions may be used. For example, alternative objective functions can be formulated in terms of maximising the log likelihood that the estimated pattern of neural activity matches the target pattern.

The optimisation problem is non-linear in a and generally is non-convex and has many local minima. Consequently, in some applications, algorithms that are likely to find only the local minima may be used. In this situation, a performance criterion is whether the optimisation algorithm delivers predicted patterns of neural activity that are a better match to the target pattern other the state-of-the art algorithms.

Any suitable algorithms for non-linear optimisation may be used, such as.

Trust Region Reflective Algorithm: Handles large scale non-linear optimisation with simple bounds on the $a_i$, such as $|a| \leq a_{max,i}$, as discussed above.

Levenberg-Marquardt Algorithm: Handles large scale non-linear optimisation, but not constraints.

In the following example, the Trust Region Reflective Algorithm is used by the controller 114 to determine the stimulation parameters, a*. The algorithm may be as implemented using any suitable computer programming languages, such as MATLAB. The Trust Region Reflective Algorithm includes the following:

(1) Pre-calculate the model basis functions $\{V_{m_a,n}^{\pm}(x)\}$. See block 210 in FIG. 2, and blocks 410 to 450 in FIG. 4.

(2) For each stimulation parameters $a_k$:
  (a) Determine the target spatial pattern of neural activity $\bar{v}^*(x)$.
  (b) Determine a locally optimal set of stimulus current $a_k^*$ using, for example, the Trust Region Reflective Algorithm using the objective function in Eq. (33) and the constraints in Eq. (31). In the objective function, the mean spike rates $\bar{v}(x|a)$ and $\bar{v}_{AP}(x|a)$ are calculated according to blocks 460 to 470 in FIG. 4.

Electrical Stimulation 230

Once the optimal stimulation parameters a* are determined, the stimulation parameters are applied to the array of electrodes 112 to provide electrical stimulation to the target neural tissue. See block 230 in FIG. 2.

Since the stimulation parameters a* are determined to optimise the difference between the (i) target spatial pattern of neural activity and the (ii) estimated spatial pattern of neural activity, (ii) approximately matches with (i).

Figure 5:
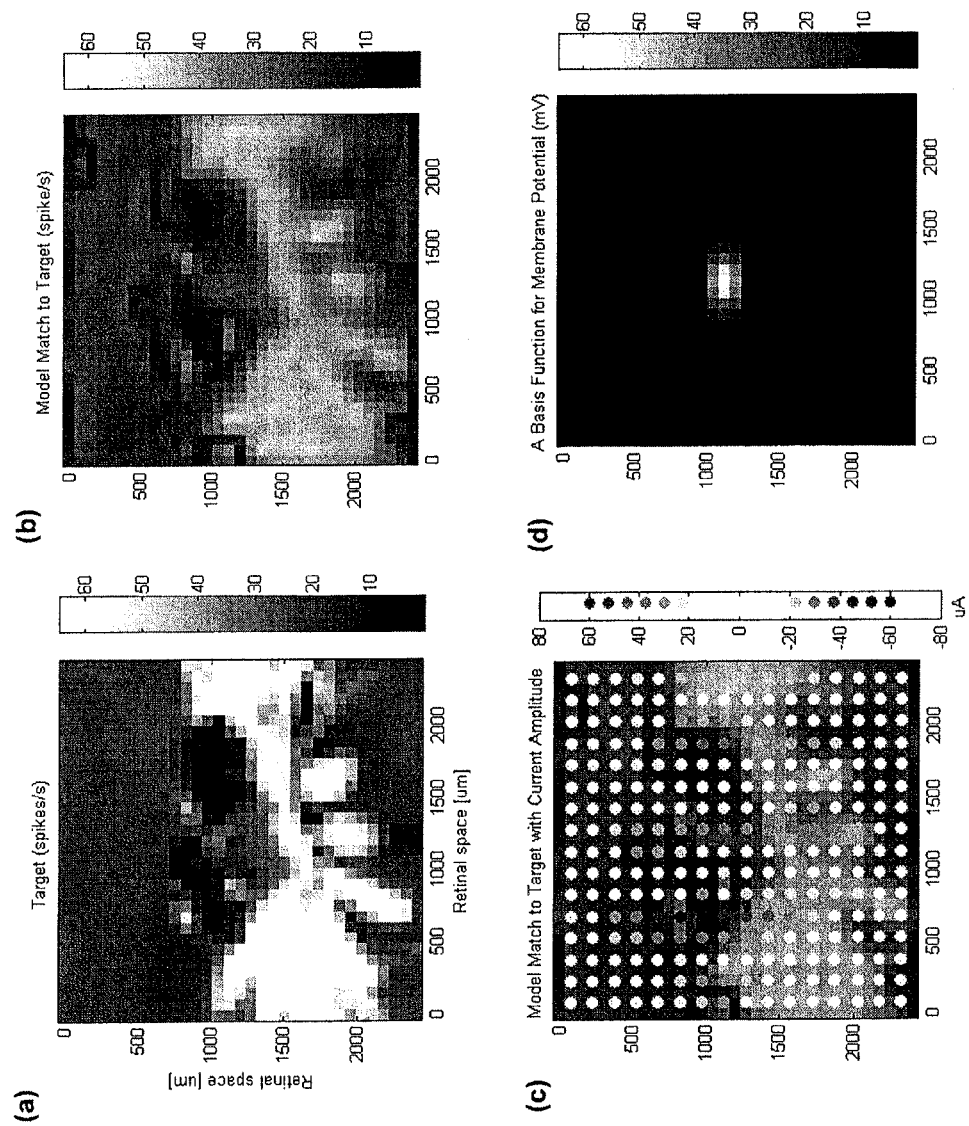
FIG. 5($a$) is an example target spatial pattern of neural activity, FIG. 5($b$) is an example of (ii) estimated spatial pattern of neural activity, FIG. 5($c$) is FIG. 5($b$) overlaid with the stimulation parameters, and FIG. 5($d$) is an example of a basis function for membrane potential.

An example for retinal stimulation using an array of 16×16 electrodes for the retina is shown in FIG. 5. In more detail:

FIG. 5(a) is an example of (i) desired spatial pattern of neural activity measured using spike rate.

FIG. 5(b) is an example of (ii) estimated spatial pattern of neural activity determined by optimising the difference between (i) and (ii) according to block 220 in FIG. 2.

FIG. 5(c) is an example of the (ii) estimated spatial pattern of neural activity in FIG. 5(b), overlaid with the stimulation parameters. In this case, the stimulation parameters are electrode amplitudes but as mentioned, other types of stimulation parameters may be used.

FIG. 5(d) is an example of a basis function for membrane potential determined at block 210 in FIG. 2. The basis function is pre-calculated to facilitate faster optimisation at block 220 in FIG. 2

In one example, the spike rate in FIG. 5(a) is determined based on image data from a camera. For example, a vision impaired user of the neuroprosthetic device wears a pair of classes with an integrated forward facing camera. The aim 1s a perception evoked by electrically stimulating the retina that is similar to what a user without the visual impairment would see.

Using pixel brightness values directly as desired spatial pattern of neural activity may lead to inaccuracies since the relationship between light intensity entering the eye and the neural activity of the neural tissue of a healthy human eye is complex.

An example of (i) a desired spatial pattern of neural activity is the pattern evoked across the retina in retinal ganglion cells (RGC) by natural light stimulation from a scene. This can be approximated capturing the scene continuously using a digital camera mounted on glasses. The spatial pattern RGC activity can be then approximated by passing the captured images through a model of RGC activity under normal visual stimulation (i.e. with light).

Model of Light Stimulation

A linear-nonlinear (LN) model of RGC response to light stimulation can be used (E. J. Chichilnisky, A simple white noise analysis of neuronal light responses, Network: Comput. Neural Syst. 12:199-213, 2001). The model involves two stages. The first, linear stage is a spatial and temporal filtering of the visual stimulus, which models the synaptic filtering that gives rise to the receptive field properties of the RGC. Physiologically, the filter may be interpreted as the receptive field of the neuron, and the filter output may be interpreted as the sub-threshold membrane potential prior to the initiation of voltage-gated ion channels associated with action potential initiation.

The second, nonlinear stage accounts for spike generation by applying a nonlinear threshold function to the output for the first stage. This captures the neural spike rate as a function of depolarizing drive: the drive must reach a minimum threshold before spike occurs; above this level, increased drive leads to an increasing spike rate up to some saturation level.

A key advantage of this form of model is that there are experimental protocols for accurately estimating the linear filters and nonlinearity using reverse correlation and maximum likelihood methods (Chichilnisky, 2001 cited above; Nicholas A. Lesica,* Jianzhong Jin, Chong Weng, Chun-I Yeh, Daniel A. Butts, Garrett B. Stanley, and Jose-Manuel Alonso, Adaptation to Stimulus Contrast and Correlations during Natural Visual Stimulation, Neuron, 55, 479-491, 2007, 2007; Sheila Nirenberg, Illya Bomash, Jonathan W. Pillow and Jonathan D. Victor, Heterogeneous Response Dynamics in Retinal Ganglion Cells: The Interplay of Predictive Coding and Adaptation, J Neurophysiol 103:3184-3194, 2010).

One of these methods involves recording the RGC response to a long sequence of pixelised images, in which the brightness of each pixel is chosen randomly at every frame from a Gaussian distribution. The spatio-temporal filter corresponding to the neuron's receptive field is recovered by calculating the cross-correlation in time between the recorded spike train and the sequence of pixelised image frames.

The nonlinearity is recovered by creating a histogram of the number of spikes that occurred as a function of the filtered output value. Alternative methods that maximise the likelihood of predicting the recorded spike train allow the LN model to be fitted to data based on stimuli other than Gaussian white noise, such as natural scenes.

These models can be applied to image data from the camera in real time in order to determine (i) the desired spatial pattern of neural activity at a suitable frame rate, such as 25 frames per second. The desired spatial pattern of neural activity may be stored on a datastore, such as RAM, and then retrieved to optimise the difference between (i) the desired spatial pattern of neural activity and (ii) the estimated spatial pattern of neural activity.

Neuroprosthetic Device 110

Figure 6:
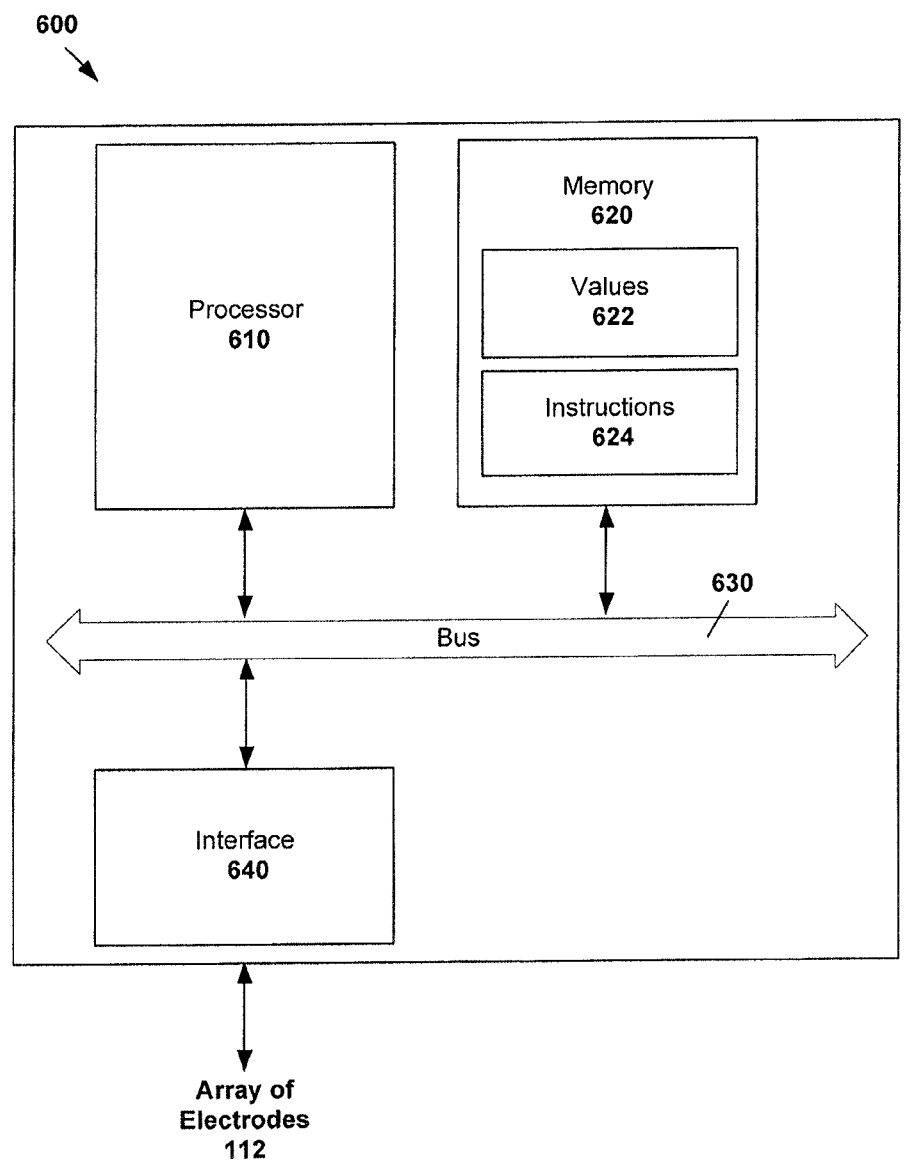
FIG. 6 is a schematic diagram of an example structure of the controller in FIG. 1.

The above examples can be implemented by hardware, software, firmware or a combination thereof. Referring to FIG. 6, an example controller 114/600 of the neuroprosthetic device 110 in FIG. 1 is shown.

The example controller 600 includes a processor 610, a memory 620 and an interface 640 that communicate with each other via bus 630. The processor 610 is for determining stimulation parameters for the array of electrodes 112 according to the examples explained above.

The memory 620 stores values 622 pre-calculated according to block 210 in FIG. 2 and blocks 410 to 470 in FIG. 4. The memory 620 also stores machine-readable instructions 624 to cause the processor to determine stimulation parameters for the array of electrodes 112 according to the examples explained above.

The interface 640 interfaces with the array of electrodes 112 to deliver stimulation parameters determined by the processor 610.

It should be understood here that the term 'processor' is to be interpreted broadly to include a CPU, processing unit, ASIC, logic unit, or programmable gate array, etc. The processes, methods and functional units may all be performed by a single processor 610 or split between several processors (not shown in FIG. 6 for simplicity); reference in this disclosure or the claims to a 'processor' should thus be interpreted to mean 'one or more processors'.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

It will be appreciated that numerous variations and/or modifications may be made to the processes, methods and functional units as shown in the examples without departing from the scope of the disclosure as broadly described. The examples are, therefore, to be considered in all respects as illustrative and not restrictive.

The invention claimed is:

1. A method comprising:
   determining, by a controller of a neuroprosthetic device, stimulation parameters for the neuroprosthetic device based on (i) a desired spatial pattern of neural activity, determining stimulation parameters for an array of electrodes of the neuroprosthetic device such that a difference between (i) the desired spatial pattern of neural activity and (ii) an estimated spatial pattern of neural activity is optimised and the estimated spatial pattern of neural activity is an estimate of a response of a target neural tissue to being stimulated by the neuroprosthetic device based on the stimulation parameters, determining the stimulation parameters further comprises estimating the response of the target neural tissue to being stimulated by the neuroprosthetic device based on the stimulation parameters using a model of how electrical stimulation evokes a spatial pattern of neural activity; and
   delivering by the controller, the stimulation parameters to the array of electrodes.

2. The method of claim 1, wherein determining the stimulation parameters comprises optimising a non-linear objective function to optimise the difference between (i) the desired spatial pattern of neural activity and (ii) the estimated spatial pattern of neural activity.

3. The method of claim 2, wherein optimising the objective function comprises minimising error or mean squared error in a measure of neural activity associated with the difference between (i) the desired spatial pattern of neural activity and (ii) the estimated spatial pattern of neural activity.

4. The method of claim 2, wherein optimising the objective function comprises maximising a likelihood function of (ii) the estimated spatial pattern of neural activity substantially matching with (i) the desired spatial pattern of neural activity.

5. The method of claim 2, wherein the stimulation parameters are determined subject to one or more constraints including one or more of:
   a threshold relating to voltage compliance is not exceeded;
   a threshold relating to charge per phase and/or charge density is not exceeded;
   a threshold relating to power limits is not exceeded;
   a threshold relating to current amplitude is not exceeded;
   a threshold relating to pulse duration is not exceeded;
   a threshold relating to inter-phase gap is not exceeded; and
   axons of passage in the target neural tissue not stimulated.

6. The method of claim 1, wherein determining the stimulation parameters further comprises estimating the response of the target neural tissue to being stimulated by the neuroprosthetic device based on the stimulation parameters using a linear-non-linear model.

7. The method of claim 6, wherein the response of the target neural tissue to being stimulated by the neuroprosthetic device based on the stimulation parameters is estimated using the linear-non-linear model by performing:
   a linear step, in which a spatio-temporal function is determined as a linear function of the stimulation parameters; and
   a non-linear step, in which using spatio-temporal pattern of neural activity is determined using the result of the linear step by passing the linear spatio-temporal function through a static non-linearity.

8. The method of claim 6, wherein the response of the target neural tissue to being stimulated by the neuroprosthetic device based on the stimulation parameters is estimated using values of membrane potential of neurons of the target neural tissue given the stimulation parameters.

9. The method of claim 8, wherein the values of membrane potential are pre-calculated using basis functions of membrane potential, each basis function being defined such that each of its constituent functions represents the membrane potential in the target neural tissue when a single electrode is active with a standard current and the remaining electrodes with zero net current through them.

10. The method of claim 8, wherein the values of membrane potential are precalculated based on values of extracellular potential in the vicinity of the target neural tissue given the stimulation parameters.

11. The method of claim 10, wherein the values of extracellular potential are pre-calculated using basis functions of extracellular potential, each basis function being defined such that each of its constituent functions represents the extracellular potential in the vicinity of the target neural tissue when a single electrode is active with a standard current and the remaining electrodes with zero net current through them.

12. The method of claim 10, wherein the values of membrane potential and/or extracellular potential are calculated using a volume conductor model defined by a partial differential equation in space and one or more boundary conditions.

13. The method of claim 10, wherein the values of membrane potential and/or extracellular potential are calculated using a bidomain model of electrical flow.

14. The method of claim 1, wherein the stimulation parameters for the array of electrodes are amplitudes of current pulses applicable by the array of electrodes on the target neural tissue.

15. The method of claim 1, further comprising, applying stimulation by the array of electrodes wherein the stimulation applied by the array of electrodes is synchronised using identical rectangular wave, charge-balanced biphasic waveforms.

16. The method of claim 1, wherein the estimated spatial pattern of neural activity represents a mean spike count, averaged over a population of neurons in the vicinity of a spatial variable associated with the target neural tissue.

17. The method of claim 1, wherein the stimulation parameters are determined in real time to dynamically adjust the stimulation parameters according to the target spatial pattern of neural activity.

18. A non-transitory computer readable medium with an executable program stored thereon that when executed causes a computer to perform the method of claim 1.

19. A controller for determining stimulation parameters for a neuroprosthetic device, the controller comprising a processor to:
based on (i) a desired spatial pattern of neural activity, determine stimulation parameters for an array of electrodes of the neuroprosthetic device such that the difference between (i) the desired spatial pattern of neural activity and (ii) an estimated spatial pattern of neural activity is optimised and the estimated spatial pattern of neural activity is an estimate of a response of a target neural tissue to being stimulated by the neuroprosthetic device based on the stimulation parameters, the processor estimating the response of the target neural tissue to being stimulated by the neuroprosthetic device based on the stimulation parameters using a model of how electrical stimulation evokes a spatial pattern of neural activity, and delivering the stimulation parameters to the array of electrodes.

20. A neuroprosthetic device comprising:
an array of electrodes to deliver electrical stimulation to a target neural tissue of a subject according to a set of stimulation parameters; and
a controller of the neuroprosthetic device to determine the set of stimulation parameters, the controller comprising a processor to:
based on (i) a desired spatial pattern of neural activity, determine stimulation parameters for an array of electrodes of the neuroprosthetic device such that the difference between (i) the desired spatial pattern of neural activity and (ii) an estimated spatial pattern of neural activity is optimised and the estimated spatial pattern of neural activity is an estimate of a response of the target neural tissue to being stimulated by the neuroprosthetic device based on the stimulation parameters, the processor estimating the response of the target neural tissue to being stimulated by the neuroprosthetic device based on the stimulation parameters using a model of how electrical stimulation evokes a spatial pattern of neural activity and delivering the stimulation parameters to the array of electrodes.

* * * * *